United States Patent
Lacoste et al.

(10) Patent No.: US 8,974,391 B2
(45) Date of Patent: Mar. 10, 2015

(54) DEVICE FOR THERAPEUTIC TREATMENT

(75) Inventors: Francois Lacoste, Paris (FR); Thierry Pechoux, Paris (FR)

(73) Assignee: Theraclion, Paris (FR)

( * ) Notice: Subject to any disclaimer, the term of this patent is extended or adjusted under 35 U.S.C. 154(b) by 0 days.

(21) Appl. No.: 12/999,739

(22) PCT Filed: Aug. 18, 2009

(86) PCT No.: PCT/FR2009/051593
§ 371 (c)(1),
(2), (4) Date: Dec. 17, 2010

(87) PCT Pub. No.: WO2010/020730
PCT Pub. Date: Feb. 25, 2010

(65) Prior Publication Data
US 2011/0137167 A1    Jun. 9, 2011

(30) Foreign Application Priority Data

Aug. 22, 2008 (FR) ...................... 08 55674

(51) Int. Cl.
*A61B 8/00* (2006.01)
*A61N 7/02* (2006.01)
*A61B 8/08* (2006.01)
*A61B 19/00* (2006.01)

(52) U.S. Cl.
CPC ... *A61N 7/02* (2013.01); *A61B 8/08* (2013.01); *A61B 2019/5276* (2013.01)
USPC .............................................. 600/439; 601/3

(58) Field of Classification Search
None
See application file for complete search history.

(56) References Cited

U.S. PATENT DOCUMENTS

| 6,508,774 B1 | 1/2003 | Acker et al. |
| 2004/0254620 A1* | 12/2004 | Lacoste et al. ................. 607/96 |
| 2005/0187476 A1* | 8/2005 | Chomas et al. ............... 600/458 |
| 2007/0232912 A1 | 10/2007 | Chen et al. |
| 2007/0265530 A1* | 11/2007 | Hashimoto et al. .......... 600/443 |
| 2008/0051656 A1 | 2/2008 | Vaezy et al. |

FOREIGN PATENT DOCUMENTS

| JP | 2001-190587 | 7/2001 |
| JP | 2007-307188 | 11/2007 |
| JP | 2009-508649 | 3/2009 |

OTHER PUBLICATIONS

Wu et al., "Using the Acoustic Interference Pattern to Locate the Focus of a High-Intensity Focused Ultrasound (HIFU) Transducer", Ultrasound in Medicine and Biology, vol. 34, No. 1, pagens 137-146, Jan. 1, 2008, New York.

* cited by examiner

*Primary Examiner* — Unsu Jung
*Assistant Examiner* — Saurel J Selkin
(74) *Attorney, Agent, or Firm* — Shoemaker and Mattare

(57) ABSTRACT

A device for therapeutic treatment includes an acoustic transducer designed to emit power waves to treat a target, and an imaging probe designed to emit waves for providing an image representation of the target and its environment before, during and after the emission of the power waves issuing from the transducer. The probe and the transducer are integrally connected to one another other. The device also includes a display for displaying images taken by the probe, namely images at rest, taken before and/or after emission of the power waves, and interference images, taken during the emission of the power waves. The device additionally comprises a detector for detecting a change of structure of the interference images that is indicative of the efficacy of the power waves.

10 Claims, 3 Drawing Sheets

DEVICE FOR THERAPEUTIC TREATMENT

Figure 1:
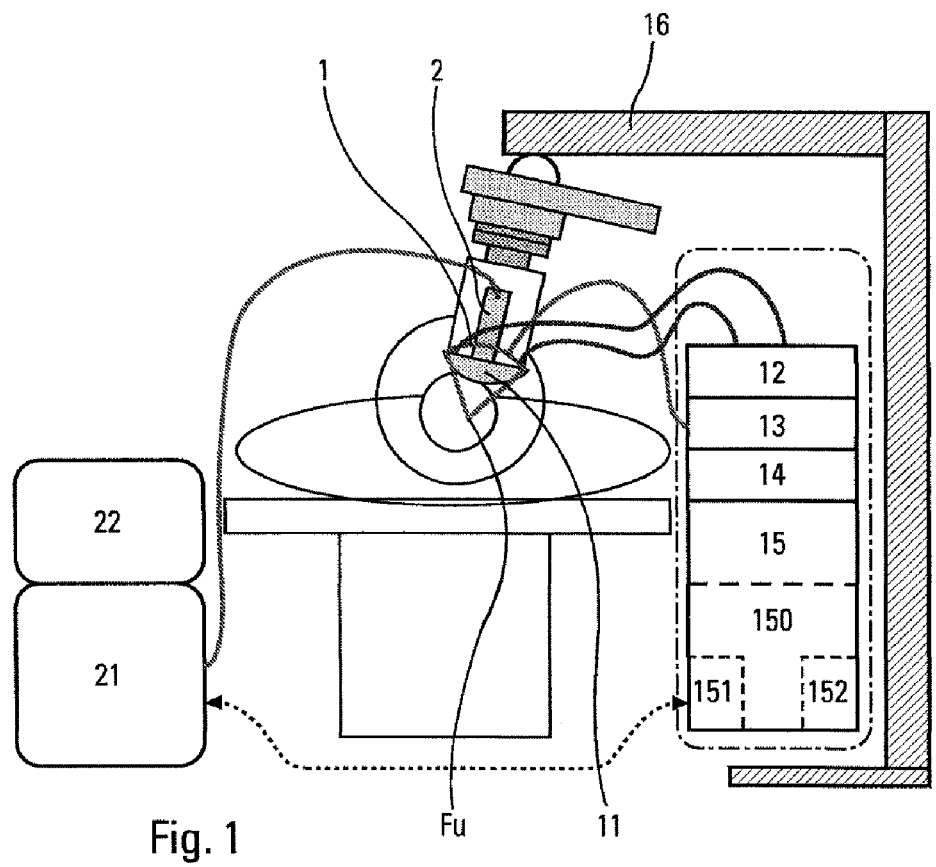

The present invention relates to the field of the treatment of living beings by ultrasound therapy devices.

In particular, it concerns treatments by focused ultrasounds (HIFU). Consequently, the present invention relates to a therapeutic treatment device, and a method for monitoring and optimizing this device.

Conventionally in the HIFU (High Intensity Focused Ultrasound) technology, an ultrasound transducer emits concentrated acoustic waves into a target tissue. These waves are absorbed by the tissue, which provokes a temperature rise in the tissue in the focal region and a coagulation of the target.

The treatment is generally performed under echography monitoring, with an echography probe mechanically linked to the transducer, as described in FR 2 886 534 for example. Thus, An online ultrasound imaging system is obtained.

The coagulation of the tissue depends on a number of factors, such as, for example:
the absorbed power (which is itself a function of the absorption of the tissue and of the in situ acoustic intensity),
the heat capacity of the tissue, and
thermal losses (by conduction, through the blood flow).

The transducer may be in direct contact with the tissue, but generally a small balloon filled with a gel or a liquid capable of transmitting the ultrasounds is used. The small balloon, by virtue of its flexibility, adapts to the shape of the tissue and facilitates the acoustic contact between the transducer and the tissue. Generally, the coupling liquid is cooled, which makes it possible to thermally protect the tissue at its interface with the device. Also generally, the fluid circulates, then making it possible to keep the temperature of the interface constant and to evacuate any bubbles.

A first problem in the ultrasound treatment of tissues is the immediate monitoring of the efficacy of the treatment of the tissues exposed to the ultrasounds, at the level of the target, but also at the level of the tissues that must be left intact, such as the interface between the device and the tissue (the skin in the case of an extracorporeal treatment) or other internal anatomical structures. Alternatively, it would be beneficial to have a monitoring of the actual temperature rise of the tissue. An insufficient ultrasound energy generally results in a target with little or poor coagulation, whereas too high an energy threatens the organs or tissues surrounding the target. However, the tissue changes induced by the high intensity ultrasounds cannot be seen with conventional echography.

As stated above, the temperature rise of the target depends on a number of factors:
the power emission of the transducer,
the transmission of the beam toward the target—and in particular the coupling between the transducer and the tissue via, for example, the skin,
the absorption of the tissue of the target,
the thermal conduction of the target,
the heat capacity and the latent heat of the tissue target.

It will therefore be understood that a method enabling monitoring the effect in the target will make it possible to detect a deviation of any one of the above factors and therefore to resolve associated technical problems.

However, there is to date no satisfactory method for non-invasively and immediately measuring the temperature on the target or changes that have taken place in the tissue. MRI can be used to ascertain the temperature of the environment, but it is a cumbersome and costly method and the reaction time of the measurement is fairly slow. Various methods for measuring the temperature by ultrasounds have been proposed, but none is satisfactory, primarily because of their high sensitivity to the movements of the patients.

A second problem is the monitoring of the correct position of the focus (area of concentration of the HIFU waves) relative to the target.

To monitor the position of the focus or the effect of the ultrasounds on the target, some authors recommend observation by an online ultrasound imaging system of hyperechoic spots in the target. These hyperechoic spots are probably created by gases generated at the focal point by the high intensity ultrasounds, either because of the cavitation induced by the acoustic field, or by the gas released by the tissue when it is raised to high temperature. This phenomenon is called "boiling". Observation of the hyperechoic spots at the focus makes it possible to some extent to monitor the treatment: in the absence of hyperechoic spots, a stronger acoustic energy will be applied, whereas the energy will be reduced if a clearly visible hyperechoic spot is observed.

However, during its emission, the high intensity beam provokes strong interferences or disturbances on the ultrasound image of the target. An interference curtain is generally produced, masking all or parts of the image, and in particular the area of the target. This interference curtain is superimposed on the image at rest (that is to say, obtained in the absence of HIFU firing) of the tissue, thus forming an interference image. The structure of this interference image is of random type and it is modified during the firing. In practice, therefore, the target is not seen or is poorly seen during the firings and the observation of the hyperechoic spots is not possible until the high intensity beam (firing) on the image at rest has been interrupted. In the prior art, a system has been proposed in which the firings and the observations on the images at rest alternate, as in the documents US20080051656, US20060264748 and US20030028111. However, this method requires the treatment to be interrupted to be able to observe the images at rest, and notably the hyperechoic spots.

At the present time, it is therefore practically impossible to monitor the firing during its emission with non-invasive and inexpensive means.

The present invention proposes a solution to the abovementioned problems by defining a treatment device and a therapy monitoring method which is noninvasive, simple, inexpensive, and does not require the interruption of the high intensity beam during the measurement.

To do this, the present invention provides for a device for therapeutic treatment comprising an acoustic transducer able to emit high intesntiy ultrasound waves toward a target in order to treat it, the power waves having a focal point, an imaging probe, such as an ecography probe, able to emit waves to provide an imaged representation of the target and of its environment, before, during and after the emission of the power waves from the transducer, the probe and the transducer being integrally linked to one another, and a display device able to display the images taken by the probe, namely images at rest taken before and/or after the emission of the power waves and interference images, taken during the emission of the high intensity waves, the focal point of the high intensity waves being situated in the imaging plane of the probe, characterized in that it also comprises detection means for detecting a change of structure of the interference images which is indicative of the effect and/or the efficacy of the high intensity waves. Unlike in the prior art, the image at rest, taken before or between firings is not observed, but the interference image during the firings is directly observed. This means that the present invention overcomes a prejudice of the prior art which assumes the interference images to be disturbed or interference-affected images that are pointless or impossible to analyze. The present invention goes against the current practice which consists in observing the images at rest in order to deduce therefrom the efficacy of the firings. With this prior art technique, the firings are very often interrupted, not because they have effectively reached their targets, but to observe on the images at rest whether they have been sufficiently effective or not. Thus, the sequence of successive firings is not determined by the efficacy of the firings, but by the search for their efficacy on the images at rest, for which the firing must be interrupted. With the present invention, the effect and/or the efficacy of the firing is monitored in real time directly on the basis of the interference images by detecting a change of structure representative of the efficacy of the firings. In other words, the invention consists in monitoring the effects of the acoustic energy in the tissues caused by the high intensity ultrasounds by observing the interference of the monitoring echography image.

According to an advantageous characteristic of the invention, the detection means may include means for measuring the brightness of the interference images. Thus, the structure of the interference images is analyzed on the basis of their brightness or luminosity, and a change of structure of the interference images will be detected from a change in brightness of these images. Advantageously, the measurement means determine a measurement area which is common to a number of interference images, and measure the average brightness in this measurement area for each interference image. This measurement area can be chosen to form all or part of the interference image. Preferably, the measurement area forms a very reduced part of the interference image, and is positioned such as to contain the anatomical site that is to be observed, such as, for example, the target or a vital organ in proximity to the target, but which must not be damaged. The measurement of the average brightness in this measurement area for each of the interference images makes it possible to assign a characteristic value to each interference image, and a characteristic change of these average brightness values will be observed which is indicative of the efficacy of the power waves from the firing.

According to a practical embodiment, the interference images are images composed of gray levels ranging from white to black, the measurement means measuring the average of the gray levels in the measurement area for each interference image. Such is notably the case when using an echography probe which delivers images in black and white consisting of gray levels.

According to another interesting characteristic of the invention, the detection means may include warning means able to trigger a warning signal when the measurement means measure a sudden rise in brightness between successive interference images. This sudden rise in brightness constitutes a change of characteristic structure of the interference images which is indicative of the efficacy of the high intensity waves. It has been found empirically that this sudden rise in brightness corresponds to the appearance of a hyperechoic spot, which can be observed on the images at rest.

The invention also defines a method for monitoring and optimizing a therapeutic treatment device comprising an acoustic transducer able to emit high intensity ultrasound waves toward a target in order to treat it, an imaging probe, such as an ecography probe, able to emit ultrasound waves to provide an imaged representation of the target and its environment, before, during and after the emission of the high intensity waves from the transducer, and a display device able to display the images taken by the probe, namely images at rest, taken before and/or after the emission of the high intensity waves and interference images, taken during the emission of the high intensity waves, the method being characterized in that it also comprises detecting a change of structure of the interference images which is indicative of the efficacy of the high intensity waves. Advantageously, the method comprises the following steps: determining, for a group of interference images that are successive in time, a measurement area which is common to the interference images of the group, and measuring the brightness of each of the interference images of the group in this measurement area. Advantageously, the measurement step may comprise measuring the average brightness in the measurement area for each of the interference images of the group. Advantageously, the interference images are images composed of gray levels ranging from white to black, the measurement step comprising measuring the average of the gray levels in the measurement area for each interference image. Preferably, the method also comprises another step consisting in detecting a sudden rise in the brightness measured between interference images that are successive in time.

The idea behind the present invention is to obtain interference images, and not images at rest, to determine in real time the efficacy of the high intensity waves of the firing. The measurement of the brightness, in particular of its average, in a determined area of the interference images, makes it possible, by a comparative analysis, to detect any change of characteristic structure indicative of the efficacy of the firing. The paradox of the present invention lies in the fact that disturbed or interference-affected images are analyzed while clean images, free of disturbances or interference, are available.

The invention will now be described more fully with reference to the appended drawings which show one embodiment of the invention as a nonlimiting example.

Figure 2:
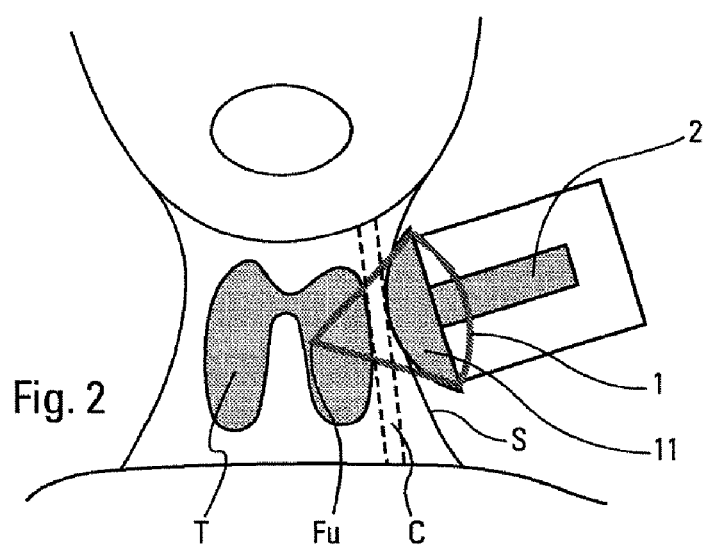
Figure 3A:
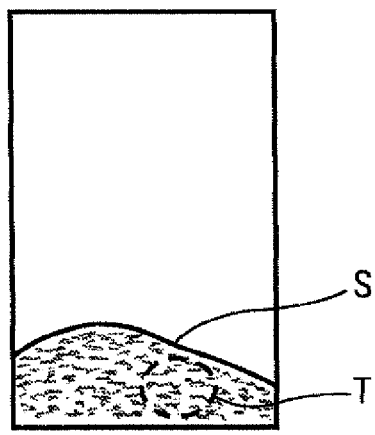
Figure 3B:
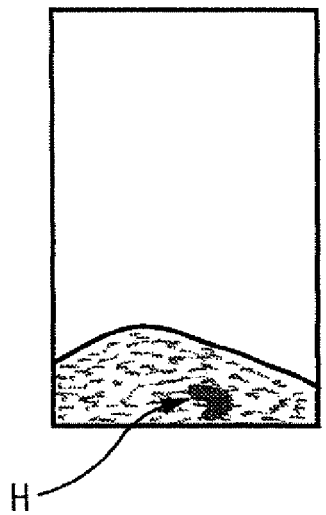
Figure 4A:
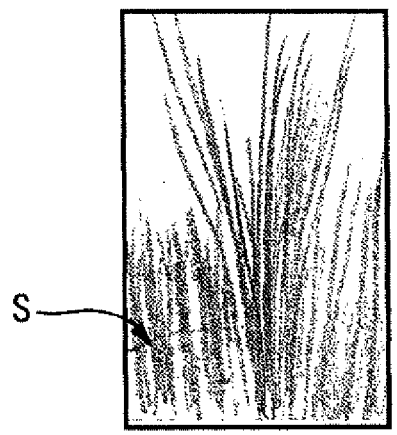
Figure 4B:
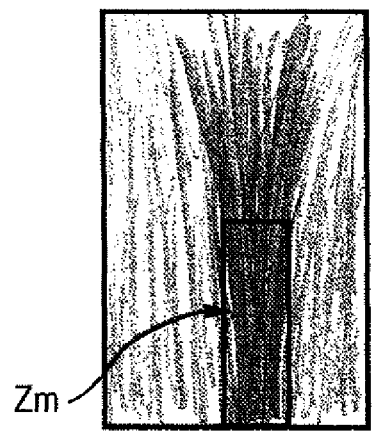
Figure 5:
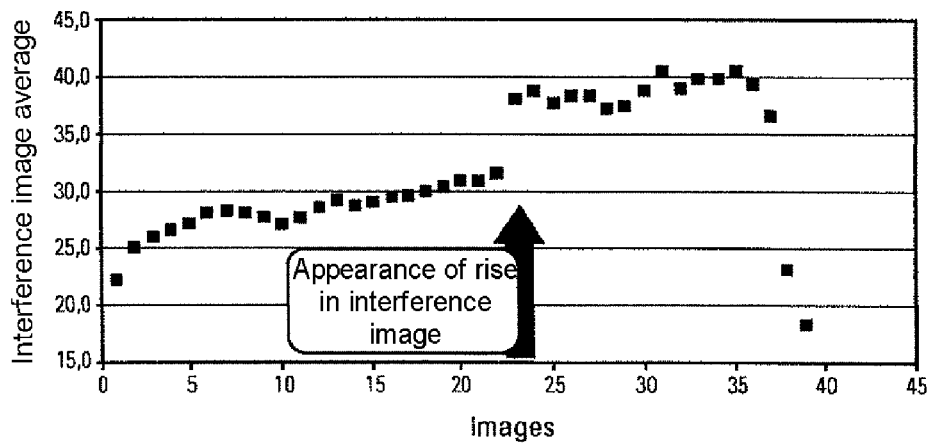
Figure 6:
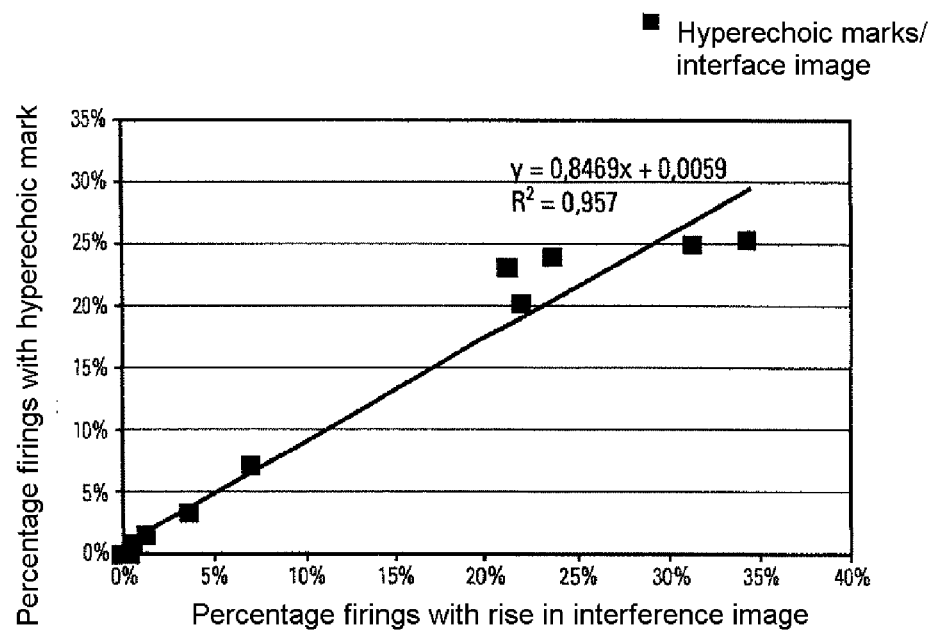

In the figures:

FIG. 1 is a schematic view of a therapeutic treatment device according to the invention, FIG. 2 is a schematic view illustrating the acoustic transducer and the imaging probe when treating the thyroid of a patient, FIGS. 3a and 3b are negative schematic representations of two images at rest, taken just after a sequence of firings, FIGS. 4a and 4b are negative schematic views of interference images taken respectively just before FIGS. 3a and 3b, FIG. 5 is a graph representing the average brightness of consecutive interference images, and FIG. 6 is another graph representing the linear relationship which exists between the rise in brightness of the interference images and the appearance of hyperechoic spots on the images at rest.

Reference will first be made to FIGS. 1 and 2 to describe in detail the various component elements of the inventive therapeutic treatment device.

The device first comprises an acoustic emission source 1 which may advantageously be an ultrasound transducer suitable for producing an ultrasound beam Fu. Preferably, the ultrasound transducer is of the HIFU focused type that makes it possible to produce a focused ultrasound beam at a precise focal point. The transducer 1, as can be seen in FIG. 2, may comprise a chamber filled with a coupling fluid through which the ultrasound beams are propagated. The chamber may, for example, be delimited by a small flexible balloon intended to come into intimate contact with an external surface S of an area of a body where a target to be treated T is located. Generally, the external surface S is the skin of the patient. To make the coupling liquid circulate within the chamber 11, circulation means 12 are generally provided, which make it possible to monitor the flow rate and the temperature of the coupling fluid inside the chamber 11. In order to work, the transducer obviously needs a power supply 13 and a displacement controller 14 that can be used to displace and accurately focus the transducer relative to the patient. For this, the transducer 1 is preferably mounted on an articulated arm 16. Finally, the transducer is coupled to a computer 15 which makes it possible to manage all the parameters of the transducer, such as its power, its frequency, its pulse time, etc.

The inventive treatment device also comprises imaging means which may, for example, be in the form of an echography probe 2 coupled to an echograph 21 and a display screen 22 which displays views or images in cross section of the anatomical site scanned by the probe 2. The probe 2 may be of the bar type. The probe 2 is mechanically coupled to the transducer 1 as can be seen in FIGS. 1 and 2. More specifically, the probe 2 and the transducer 1 are integrally linked to one another so that the probe 2 follows the focal point of the ultrasound beam Fu. The area of maximum intensity of the ultrasound beam Fu is always represented on the image on the screen 22. For this, the echograph 21 may be coupled to the computer 15 of the transducer as can be seen in FIG. 1. Preferably, the echography image is acquired by the computer via the electronic link between 21 and 151.

With an echography probe 2, the echograph 21 produces on the display screen 22 images that are successive in time of the area surrounding the focal point of the ultrasound beams Fu. These images are made up of pixels having gray levels ranging from black to white. The white pixels are representative of a very strongly echogenic element, whereas the black pixels are representative of elements with very little or no echogenic property. This is well known for echography images. The display screen 22 provides images before the emission of the power waves Fu, during the emission of the power waves, and after the emission of the power waves. In other words, echography images are available before, during and after the firings. The images taken before and after the firings are relatively clean and show the target to be treated and its anatomical environment. These images are here called "images at rest", that is to say, taken in the absence of firings. Such images at rest are schematically represented in negative in FIGS. 3 and 3b. They are in fact negative images, given that the white areas in these figures in fact appear in black on the display screen 22, and the black areas appear in white on the display screen. The bottom part of FIGS. 3a and 3b represents the tissue at the anatomical site incorporating the target T represented by dotted lines. The skin S of the patient can be clearly identified. FIG. 3b shows a hyperechoic mark H. In addition to these images at rest, the display screen also produces images corresponding to the firing phases. Because of the power imparted by the high intensity waves Fu, considerable interferences are generated which disturb or create interference in the image, so that the representation of the anatomical site, as can be seen in FIGS. 3a and 3b, is no longer or only weakly perceptible. In other words, the interferences produced by the power waves are superimposed on the image at rest, but these interferences are so strong that the image at rest is very strongly degraded. The images during the firing phases will hereinbelow be designated by the term "interference images". Such images are schematically represented in negative in FIGS. 4a and 4b. FIG. 4a was, for example, taken just before the image at rest 3a. As for the interference image of FIG. 4b, it was, for example, taken just before the image at rest of FIG. 3b. In FIG. 4a, it is very difficult to discern the outline of the skin S. The interferences which take the form of upwardly divergent beams almost entirely mask the representation of the anatomical site, as can be seen in FIGS. 3a and 3b. This is all the more notable in FIG. 4b where the interferences are particularly strong, so that the anatomical site is no longer visible at all. This is why these interference images have hitherto never been used to deduce any information as to the presence and/or the efficacy of high intensity ultrasound waves from the firing.

Now, it was surprisingly found that, when a hyperechoic spot H is produced at the focal point, the interference image is strongly modified. This is represented in FIGS. 3b and 4b, which should be compared to FIGS. 3a and 4a. As a reminder, the hyperechoic spots are attributed to the assumed formation of gas at the focus, also known as "boiling". A rise in the brightness or luminosity of the interference image was also observed. A modification of the structure of the image can also be observed: the rise in its brightness is greater in line with the tissues whose brightness (in the ultrasound imaging) increases under the effect of the therapy. Thus, the brightness of the interference image (FIG. 4b) is reinforced in the area of the image situated around the focal point precisely when a hyperechoic spot appears in this same focal area. The interest in this observation is that, during the firings, this hyperechoic spot is hidden by the interference image and therefore cannot be observed directly, whereas the modifications of the interference image are clearly visible.

FIG. 4b shows how it is possible to detect a rise in the brightness of the interference image in a predefined measurement area of the image, which is designated Zm. The brightness of the image, in other words the gray level, is measured in the area Zm. Preferably, the area Zm encompasses the focal point of the firing transducer.

The area is determined to preferably cover the part of the image that rises most during a firing provoking a hyperechoic mark. The inclusion of the entire interference image is avoided, because rises are sometimes observed in the lateral parts of the image, which are not indicative of an effective treatment. Typically, the measurement area is of elongate shape towards the transducer, which is centered laterally on the focal point, encompasses the latter, but is offset toward the transducer so as to encompass a part of the pre-focal area.

It is, however, possible to define an area Zm which does not include the focal point, for example encompassing an anatomical structure that is to be protected from the acoustic waves. In practice, it is found that a structure adjacent to the target may become hyperechoic during the treatment, which indicates that it is modified by the ultrasounds. This may be the case with the skin or subcutaneous tissues, such as the carotid C which can be seen in FIG. 2. This effect must generally be avoided and this is possible by virtue of the invention. According to the invention, the measurement area Zm is placed around the anatomical area to be protected and any rise in the interference image in this area will be monitored.

The average brightness of the gray levels in the area Zm taken during the firing can be calculated: this value firstly makes it possible to detect the presence of an interference image and therefore monitor the effective emission of the high intensity firings. The calculated value also makes it possible to detect any rise in the gray levels during an effective firing. This rise occurs notably if the interference is concentrated in the area Zm. Now, this rise in brightness, which has been found to be linked to the presence of a hyperechoic mark, reveals a change of structure of the interference image which is characteristic or indicative of the effect and/or the efficacy of the firing.

There are a number of possible methods for detecting the efficacy of the HIFU firing. In a first mode, the average is calculated pixel by pixel in the area Zm of each image taken during the firing. Each of the averages obtained on an image are then averaged in time over the duration of the firing. If the number obtained is above an experimentally determined threshold, the HIFU firing is considered effective.

In a second mode, the average is also calculated pixel by pixel in the area Zm of the image at time point of the firing, from which the pixel-by-pixel average in the area Zm of the image at a preceding time point t-dt is subtracted. If the number obtained is greater than an experimentally determined threshold, the HIFU firing is considered effective. This second mode makes it possible to interrupt the firing when the efficacy threshold is reached.

To detect a hyperechoic mark, the pixel-by-pixel difference is calculated in the area Zm of an image taken after the firing by comparison with an image taken before the firing. The maximum of this difference is then calculated. This maximum can be used as an indicator of the absence or presence of a hyperechoic mark.

FIG. 5 shows the trend of the average gray level in the area Zm during a firing, according to the second method. It can be seen that the curve shows an abrupt upward discontinuity which corresponds to a sudden rise in brightness, indicative of the presence of a hyperechoic spot, and therefore of an effective treatment.

FIG. 6 shows the results, obtained from 11 patients, with a thyroid nodule treated by HIFU. The echographic images recorded on video during the firings were analyzed a posteriori. After each firing, the presence or the absence of hyperechoic marks was detected and, during each firing, the possible sudden rise in the interference image was detected. These detections were made with the image analysis methods specified above. It can be seen that there is a very good correlation between the two types of detection.

Moreover, an almost linear correlation has also been observed between the success of the treatment and the percentage firings during which a sudden rise in the interference image is detected.

These were the same treatments of thyroid nodules by HIFU as in the preceding section. Since the aim of the treatments is to reduce the volume of these nodules, the success of the treatment is gauged by the percentage reduction of these nodules.

The measurement of the sudden rise in the interference image is therefore predictive of the success of the treatment.

In order to analyze the interference images in the manner described hereinabove, and notably to detect the change of characteristic structure of the interference images, which is indicative of the efficacy of the power waves, the therapeutic treatment device incorporates detection means 150, which can, for example, be integrated in the computer 15. These detection means may take the form of appropriate processing software. The detection means 150 include, among other things, means for measuring the brightness or luminosity 151 of the interference images. Advantageously, these interference means 151 can be used to determine the positioning and the shape of the measurement area Zm in which the average brightness for each interference image will be measured. The measurement means 151 will notably measure the average of the gray levels in the measurement area Zm for each interference image. The detection means 150 may also include warning means 152 able to trigger a warning signal when the measurement means 151 detect a sudden rise in brightness between two consecutive interference images. The warning signal may be audible or visual, for example displayed on the computer screen or on the display screen 22. The warning signal may also be coupled to a monitoring of the power supply 13 in order to interrupt or modulate the ultrasound power emitted by the transducer 1.

By virtue of the invention, it is possible to monitor in real time the presence and more particularly the efficacy of the power waves emitted, without having to interrupt the firing.

The invention claimed is:

1. A method for monitoring a therapeutic treatment device having an acoustic treatment transducer, an imaging probe and a display device, said method comprising steps of:
   emitting first acoustic waves from the acoustic transducer toward a target in order to treat the target,
   emitting second waves from the imaging probe to provide an imaged representation of the target and the target's environment, before, during and after the emission of the first acoustic waves from the transducer,
   forming images of the target from said second waves, said images including interference images from said first waves,
   displaying images of the target taken by the probe before and/or after the emission of the first acoustic waves and interference images of the target, taken during the emission of the first acoustic waves on the display device,
   detecting a change of structure of the interference images,
   monitoring any effect of the first acoustic waves by observing said change of structure, and
   detecting any rise in brightness measured between interference images that are successive in time constituting a change of structure of the interference images which is indicative of the effect of the first acoustic waves.

2. The method as claimed in claim 1, further comprising the following steps:
   determining, for a group of said interference images that are successive in time, a measurement area which is common to the interference images of the group,
   measuring the brightness of each of the interference images of the group in the measurement area.

3. The method as claimed in claim 2, wherein the measuring step comprises measuring the average brightness in the measurement area for each of the interference images of the group.

4. The method as claimed in claim 2, wherein the interference images are images composed of gray levels ranging from white to black, the measuring step comprising measuring the average of the gray levels in the measurement area for each interference image.

5. The method as claimed in claim 1, wherein the imaging probe is an echography probe.

6. A device for therapeutic treatment comprising:
   an acoustic transducer able to emit first acoustic waves toward a target in order to treat the target, the first acoustic waves having a focal point;
   an imaging probe able to emit second waves to provide images and interference images of the target and of the target's environment, before, during and after the emission of the first acoustic waves from the transducer, the probe and the transducer being integrally linked to one another in a unitary body;
   a display device able to display the images of the target taken by the probe before and/or after the emission of the first acoustic waves and interference images, taken during the emission of the first acoustic waves, the focal point of the first acoustic waves being situated in the image taken by the probe; and
   a detector for detecting a change of structure of the interference images which is indicative of any effect of the first acoustic waves;

wherein the detector is configured to measure brightness of the interference images; and wherein the detector includes a trigger configured to emit a warning signal when the brightness measuring device measures a rise in brightness between successive interference images constituting a change of characteristic structure of interference images which is indicative of the efficacy of the first acoustic waves.

7. The device for therapeutic treatment as claimed in claim 6, wherein the brightness measuring device is configured to determine a measurement area which is common to a number of said interference images, and to measure the average brightness in this measurement area for each interference image.

8. The device for therapeutic treatment as claimed in claim 7, wherein the interference images are images composed of gray levels ranging from white to black, and the brightness measuring device is configured to measure the average of the gray levels in the measurement area for each interference image.

9. The device for therapeutic treatment as claimed in claim 6, wherein the warning signal is coupled to the transducer in order to stop the warning signal or modulate the warning signal's power.

10. The device as claimed in claim 6, wherein the imaging probe is an echography probe.

* * * * *